(12) United States Patent
Kelson et al.

(10) Patent No.: US 6,202,843 B1
(45) Date of Patent: Mar. 20, 2001

(54) COOPERATIVE MEDICAL SAMPLING AND NEEDLE REMOVAL DEVICES

(76) Inventors: Lance P. Kelson, 300 N. 5555 West; Ross J. Kelson, 436 N. 5550 West, both of Ogden, UT (US) 84404

( * ) Notice: Subject to any disclaimer, the term of this patent is extended or adjusted under 35 U.S.C. 154(b) by 0 days.

(21) Appl. No.: 08/577,873

(22) Filed: Dec. 22, 1995

Related U.S. Application Data

(63) Continuation-in-part of application No. 07/901,922, filed on Jun. 22, 1993, now Pat. No. 5,531,323.

(51) Int. Cl.[7] ......................................... B65D 83/10
(52) U.S. Cl. ................................. 206/366; 206/370
(58) Field of Search .................... 206/635, 366, 206/365, 370; 604/192, 110; 220/908; 29/235

(56) References Cited

U.S. PATENT DOCUMENTS

| | | | |
|---|---|---|---|
| 4,375,849 | * | 3/1983 | Hanifl ................................. 206/366 |
| 4,667,821 | * | 5/1987 | Shillington ........................ 206/366 |
| 4,738,362 | * | 4/1988 | Burns et al. ...................... 206/366 |
| 4,892,191 | * | 1/1990 | Nakamura ......................... 206/366 |
| 4,986,811 | * | 1/1991 | Thead et al. ...................... 206/366 |
| 4,989,307 | * | 2/1991 | Sharpe et al. .................... 206/366 |
| 5,067,223 | * | 11/1991 | Bruno .............................. 29/426.5 |
| 5,187,850 | * | 2/1993 | McCammon et al. ............ 206/366 |
| 5,474,181 | * | 12/1995 | Shillington et al. .............. 206/366 |
| 5,531,323 | * | 7/1996 | Kelson et al. .................... 206/366 |

* cited by examiner

Primary Examiner—David T. Fidei
(74) Attorney, Agent, or Firm—Mallinckrodt & Mallinckrodt; Brian R. Rayve; Robert R. Mallinckrodt

(57) ABSTRACT

Devices for manually removing and disposing of blood sampling needles after use, with a minimum of manipulation and without manual contact with any contaminated part. The manual needle removal devices disclosed are incorporated into the lids of needle disposal containers. After insertion of the used needle assembly into the device, only rotary motion is needed to unscrew it to allow it to fall into the container.

1 Claim, 13 Drawing Sheets

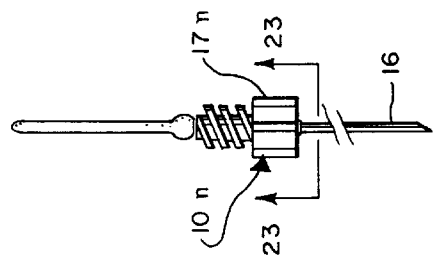
FIG. 22  FIG. 23
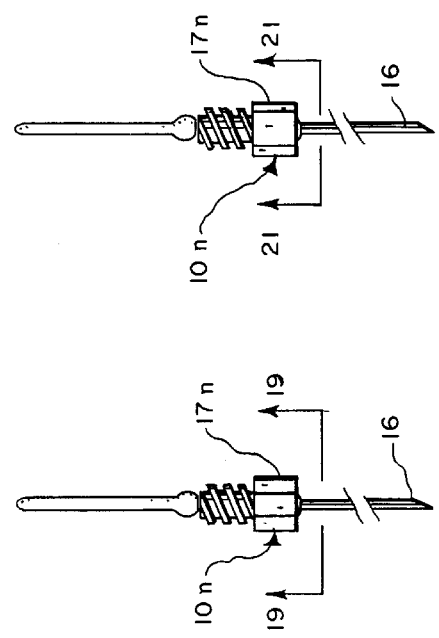
FIG. 20  FIG. 21
FIG. 17  FIG. 18  FIG. 19
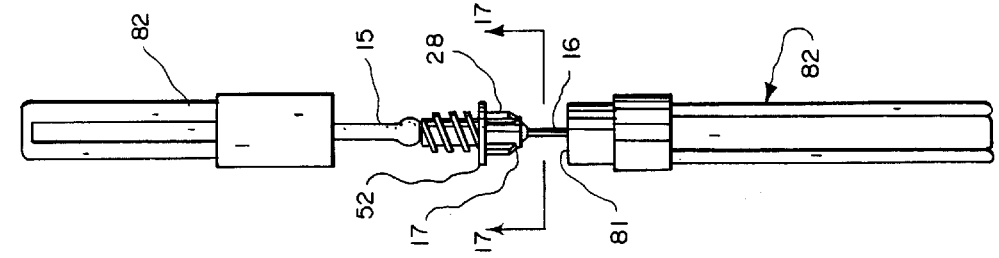
FIG. 16

COOPERATIVE MEDICAL SAMPLING AND NEEDLE REMOVAL DEVICES

RELATED APPLICATIONS

This application is a continuation-in-part of application, Ser. No. 07/901,922, filed Jun. 22, 1993, for COOPERATING MEDICAL SAMPLING AND NEEDLE REMOVAL DEVICE, now U.S. Pat. No. 5,531,323.

1. FIELD

The field of the invention is the safe disposal of medical needles used to withdraw body fluids, and more particularly the disposal of such needles and associated contaminated items.

2. STATE OF THE ART

Several manually and electrically powered devices have been proposed for the destruction of used syringe needles. Some destroy only the cannula (needle), shearing it off and depositing it into a receptacle for discard. Others also destruct the plastic hub of the needle and portions of the syringe barrel. See U.S. Pat. Nos. 3,469,750, 4,255,996, 3,851,555 and 4,275,628. All provide receptacles for the severed needles, hubs and other destroyed parts of the syringe. The contaminated syringe bodies must be separately placed in the disposal receptacles when these devices are used, although U.S. Pat. No. 3,469,750 refers to a device which crushes the entire syringe assembly. It is noted that this device is very heavy, stationary and not portable. The large force required is felt to be potentially dangerous.

Blood samples are now generally taken not with syringes for subsequent transfer to a sample container such as a test tube, but directly into such a container. This container is evacuated, sealed by an elastic plug, and placed seal first into an elongate barrel sleeve open at one end and narrowed to a threaded nipple at the other. A double ended tubular sampling needle (cannula) is mounted on a central hub threaded to fit the nipple. The outside end of the cannula is inserted into a vein. The sealed end of the evacuated container is then pressed against the other, inside, end of the needle, puncturing the resilient plug and allowing the internal vacuum to draw the blood sample through the needle into the container. After the needle is withdrawn from the vein, the container is withdrawn from the needle, leaving the sample inside. The sleeve may be safely reused since it never contacts the blood or the body of the patient. However, there is presently no method of removing the needle from the barrel without excessive manipulation and attendant danger of injury and infection to the medical technician. Typically, a needle disposal receptacle is provided with a lid having an aperture shaped to engage the needle hub. See U.S. Pat. No. 4,375,849. The technician, who most often has one hand engaged with the patient's needle wound, must very carefully insert the needle into the narrow opening with the other. Then, he must grip, release and regrip the sleeve several times while rotating it to unscrew it from the needle hub, all with a single hand. It is difficult to perceive when the needle is completely disengaged, and the needle even then tends to hang up in the opening. Danger of injury from the contaminated needles is considerable.

U. S. Pat. Nos. 4,667,821 and 4,738,362 add needle gripping wrenches to the lids, but do not facilitate removal with only one hand. U.S. Pat. Nos. 4,807,344 and 4,862,573 disclose motorized devices permitting one-handed needle removal, but the devices tend to be overly expensive.

The difficulty of disposing of the used needle assembly without manual contact is increased substantially by the configuration of state of the art medical sample needle assemblies. The assemblies have a hub with a flange which is larger in diameter than both the threads and the wrenching or gripping area therebelow. Clearly, state of the art medical sampling needle assemblies with hubs so configured tend to become suspended from any removal tool, whether manually or otherwise powered, rather than falling freely therethrough into the disposal receptacle.

A great need remains for an economical needle removal system allowing facile, safe, one-handed needle removal and disposal.

BRIEF SUMMARY OF THE INVENTION

With the foregoing in mind, the present invention eliminates or substantially alleviates the shortcomings and disadvantages of the prior art by removing virtually all the manual manipulation now required to remove and dispose of double ended fluid sampling needles used with evacuated sample containers. The device comprises a rotating wheel adapted to engage the hubs of the needles, an electrical motor to provide torque to the wheel, either directly or through appropriate gears, and electrical switching and control means. Advantageously, these components are all mounted upon a base adapted to be secured to the mouth of a disposal receptacle for the used needles. After the specimen container is removed, the container sleeve is positioned in the device, the needle and hub being inserted through an aperture provided through the base. The hub is then unthreaded from the sleeve by the wheel, and then drops into the receptacle.

In the preferred embodiment, the rotating wheel is powered by a two phase unidirectional stepper motor, along with a pulse generating tinier circuit and motor controller (chip). The stepper type motor is preferred because it builds very quickly to full torque, and also because it stops promptly without appreciable coasting when electric power to it is interrupted. The needle engaging periphery of the wheel may be recessed in at least one location to provide clearance for inserting the needle for removal. A spring loaded, normally open, initiation switch is pressed by the vacuum container sleeve to start the motor. A cam operated cycle control switch assures that the motor is always stopped with the wheel in proper position for the next use. Parallel arrangement of the initiation and cycle control switches assures the continued operation as long as the former is held in depressed, closed position. Direct current batteries are provided in one embodiment. In another, a transformer/rectifier is used with an alternating current source. Batteries, is used, may be mounted upon the above mentioned plate. In this case, it is advantageous to employ rechargeable batteries and appropriate recharging circuitry. Since needle hubs commonly carry cruciform, gear-like knurls, the hub engaging wheel advantageously carries cogs on its circumference, although knurls or other high friction constructions may also be used.

In another preferred embodiment, a standard direct current motor is employed, again with batteries or a transformer/rectifier with AC source. Recharging circuitry is advantageous with this embodiment also.

It is therefore the principal objective of the invention to provide a device for the disposal of used medical cannulae without danger of injury or infection to the medical technician, nurse or doctor.

The herein claimed invention eliminates or substantially alleviates the shortcomings and disadvantages in state of the art medical sampling and needle removal devices, by providing a needle assembly which facilitates its removal from body fluid sampling assemblies without manual contact. The needle assembly comprises a cannula mounted within a hub having an uppermost portion threaded to engage the internally threaded nipple of the barrel sleeve. The threaded portion is integral with a lowermost portion, which is configured to be gripped on at least a portion of its surface for installation into and removal from the nipple. The hub is configured so that no point on the portion of its surface used for gripping is radially nearer to the cannula than is any other point thereabove on the surface of the hub. This is to assure that the needle, when unscrewed from the nipple, may fall freely into a used needle receptacle without hanging up on whatever removal tool may be employed. Preferably, the gripping surface is significantly more distant from the cannula than any other point on the hub, to provide ample clearance.

The invention further provides a cooperating lid for a needle disposal container, designed to grip the needle hub and to support the sleeve to provide facile one-landed rotation of the sampling assembly sleeve to unscrew the needle.

In accordance with other preferred embodiment of the invention, such a cooperating lid is adapted for use with state-of-the-art, unaltered conventional medical sampling needle assemblies.

It is therefore the principal object of the herein claimed invention to provide a cooperating medical sampling needle assembly and a disposal container lid adapted to facilitate needle removal and disposal.

BRIEF DESCRIPTION OF THE DRAWING

In the drawings, which represent the best mode presently contemplated for carrying out the invention.

DETAILED DESCRIPTION OF ILLUSTRATED EMBODIMENTS

Figure 1:
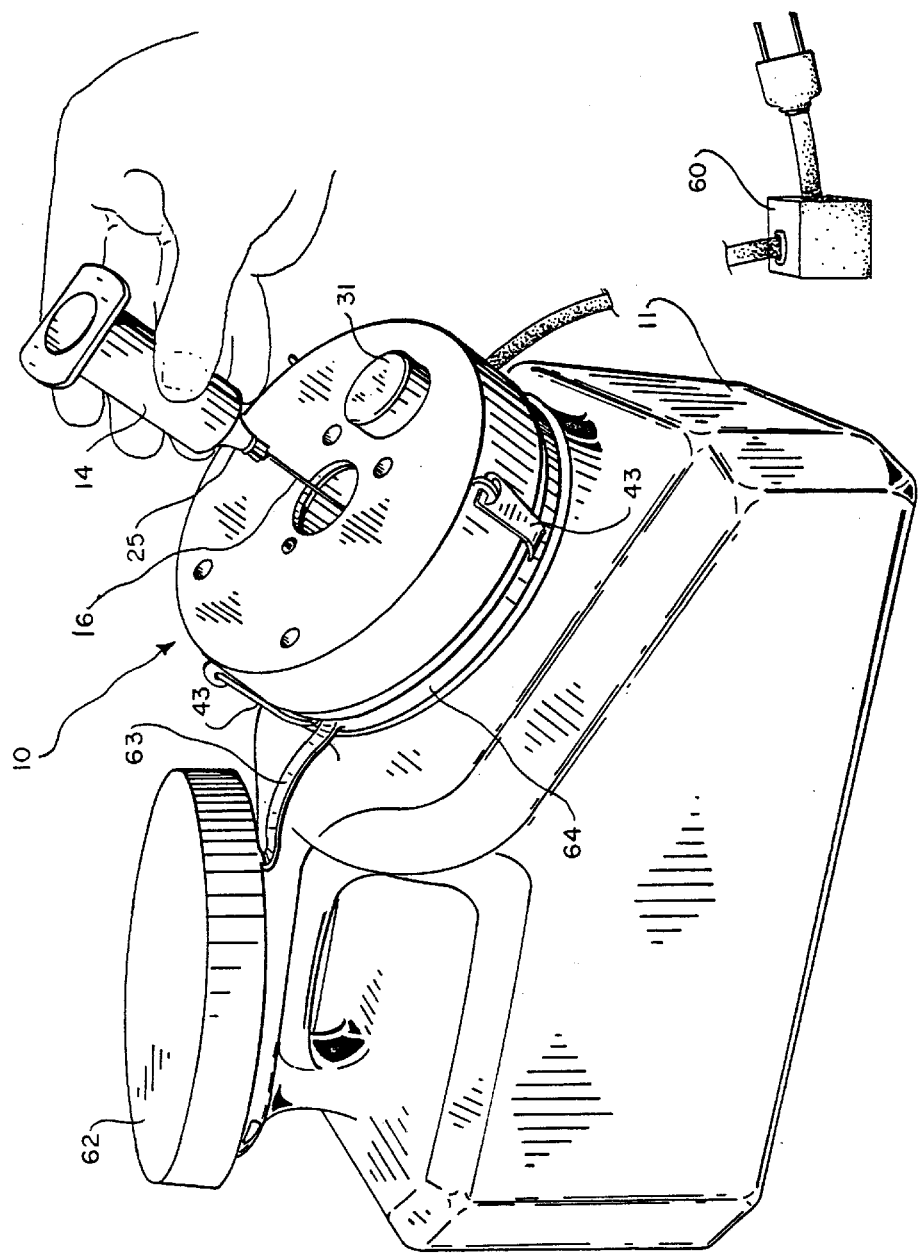
FIG. 1 is a perspective view of the needle remover and disposal device secured to the mouth of a needle disposal receptacle, drawn to a somewhat reduced scale, FIG. 2 a blood sample taking assembly including an evacuated sample container, a double-ended cannula and the sleeve initially holding the sample container, partially cut away, drawn to substantially full scale, FIG. 3 a vertical cross sectional view of the needle removal device of FIG. 1, taken along line 3—3 thereof, and including the sample container sleeve and the double-ended cannula being removed therefrom, drawn to substantially full scale, FIG. 4 a vertical sectional view of a fragment of the needle remover of FIG. 6, taken along line 4—4 thereof, showing the cycling switch and the associated cam, drawn to substantially full scale, FIG. 5 a top view of the needle remover of FIG. 3, taken along line 5—5 thereof, the cover being cut away to show the control panel, the batteries, and the cycle control switch, drawn to substantially full scale, FIG. 6 a sectional view taken along line 6—6 of FIG. 5, drawn to the same scale, FIG. 7 a view of the bottom of the needle remover of FIG. 3, taken along line 7—7 thereof, drawn to the same scale, FIG. 8 a view of the top of the cog wheel of FIG. 6, taken along 8—8 thereof, drawn to the same scale, FIG. 9 an enlarged view of a fragment of FIG. 7 showing the cogs in engagement with the knurls of the needle hub, FIG. 10 a schematic view of the power and control system operating the motor of the needle removal device, FIG. 11 a schematic representation of an alternate system of cogs or wheels to unscrew the needle from the sleeve, FIG. 12 a bottom plan view of another preferred embodiment of needle remover 10, drawn to substantially full scale, FIG. 13 a bottom plan view of the needle remover of FIG. 12, the cover thereof partially cut away, drawn to the same scale, FIG. 14 a side elevation view of the needle remover of FIG. 13, taken along line 14—14 thereof, partially sectioned along the same line, drawn to the same scale, FIG. 15 a schematic representative of the power and control system operating the motor of the needle remover, FIG. 16 a view of a state of the art needle assembly, drawn to a somewhat enlarged scale, shown partially withdrawn from its protective storage case, FIG. 17 a cross sectional view of the needle of FIG. 16, taken along line 17—17 thereof, drawn to the same scale, FIG. 18 a view of a medical needle assembly in accordance with the invention, shown fragmentally, having a hexagonally shaped hub, drawn to the scale of FIG. 17, FIG. 19 a cross sectional view of. the needle assembly of FIG. 18, taken along line 19—19 thereof, drawn to the same scale, FIG. 20 an elevation view of another embodiment of the inventive medical needle, the hub thereof being round accept for a pair of opposed wrenching flats, drawn to the scale of FIG. 17, FIG. 21 a cross sectional view of the needle assembly of FIG. 20, taken along line 21—21 thereof, drawn to the same scale, FIG. 22 an elevation view of a fragment of still another embodiment, having a radially ribbed wrenching portion of the hub, drawn to the scale of FIG. 17, FIG. 23 a cross sectional view of the needle assembly of FIG. 22, taken along line 23—23 thereof, drawn to the same scale, FIG. 24 an elevation view of a fragment of a further embodiment, having flutes.extended beyond an upper disc, drawn to scale of FIG. 17, FIG. 25 a cross sectional view of needle assembly of FIG. 24, taken along line 25—25 thereof, drawn to the same scale, FIG. 26 a vertical sectional view of a fragment of a disposal container lid with the needle removal device thereof in use, drawn to substantially full scale, FIG. 27 a top plan view of the fragment of FIG. 26, drawn to the same scale, FIG. 28 a vertical sectional view of the fragment of the lid of a needle disposal device showing the needle removal portion thereof, in conjunction with a conventionally shaped needle and hub, drawn to approximately two times scale, FIG. 29 a bottom plan view of the fragment of FIG. 28, taken along line 29—29 thereof, drawn to the same scale, FIG. 30 a fragment of a lid of a disposal container having a sloping opening, showing the needle removal portion thereof, drawn to the-scale of FIG. 28, FIG. 31 a vertical sectional view of a fragment of the lid of a needle disposal device showing the needle removal portion thereof for a conventionally shaped needle and hub, with a pin wrenching member, drawn to the scale of FIG. 28.
Figure 2:
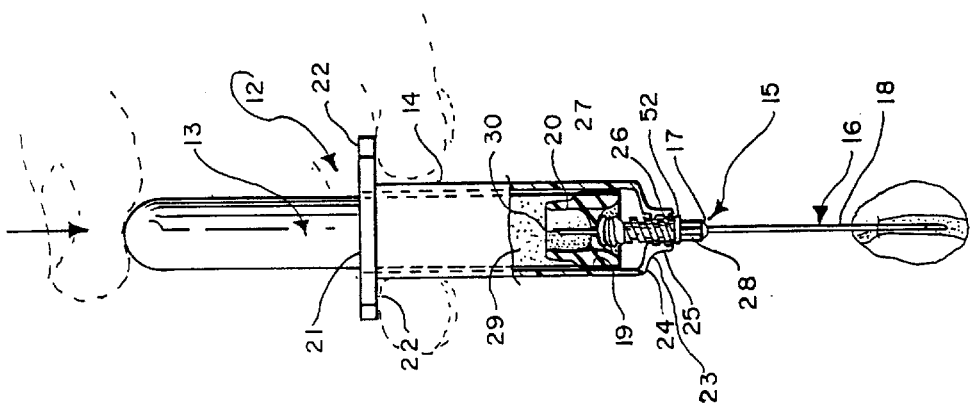

In FIG. 1, needle remover 10 is secured in place of a lid upon a used-needle receptacle 11. An assembled vacuum container blood sampling device 12 is shown in FIG. 2. Sampler assembly 12 comprises an evacuated specimen container 13, a container sleeve 14, and a sampling needle assembly 15. Needle assembly 15 includes double-ended tubular cannula 16 secured within a central hub 17. Outside portion 18 of cannula 16 is indicated as inserted into a vein. The evacuated sample container 13 is closed at its open end 19 by an elastic seal 20, preserving the internal vacuum until time of use. Sleeve 14 has an open end 21 with a pair of graspable ears 22. Its opposite end 23 narrows through a shoulder 24 of a nipple 25 with internal threads 26. Threads 26 accept external threads 27 on hub 17. Hub 17 is typically provided with cruciform knurls 28, which are gripped to engage hub 17 to nipple 25.

Figure 3:
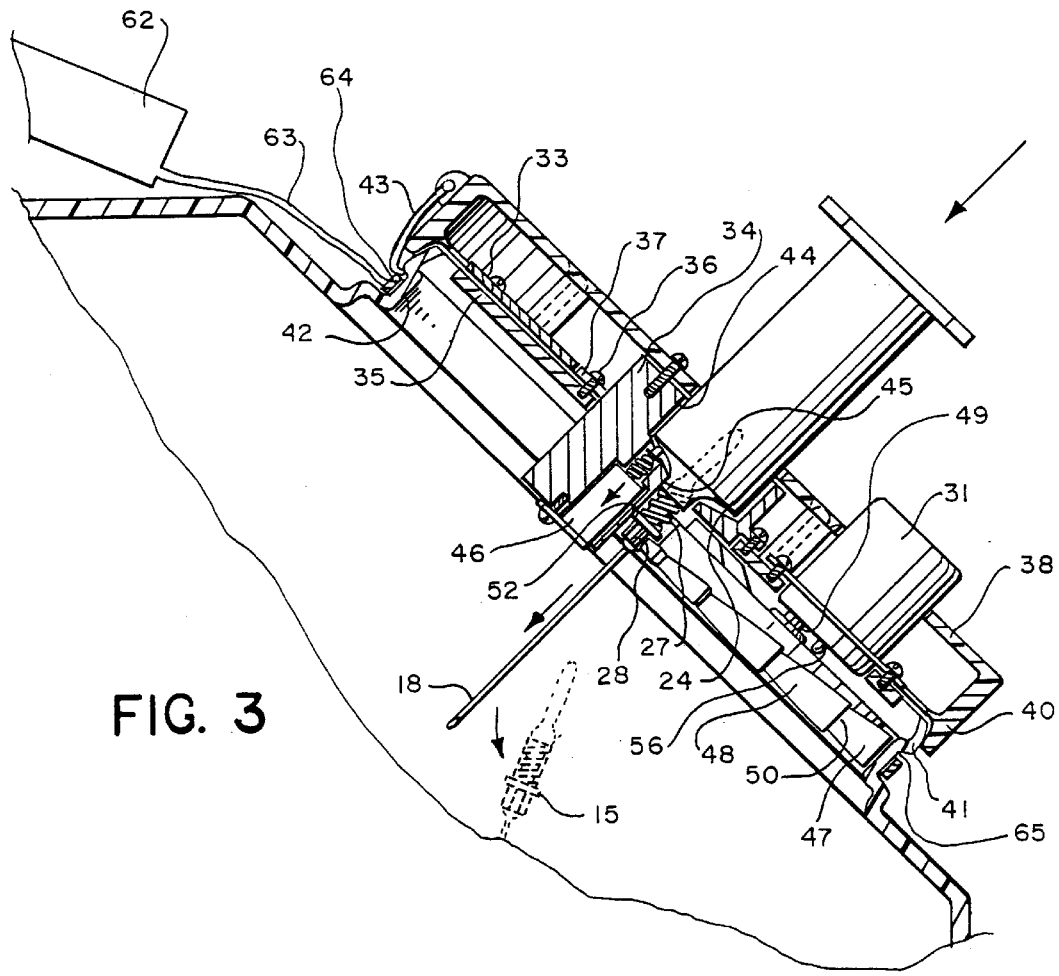

To take a blood specimen 29, outside needle 18 is first inserted into the vein. Then, vacuum container 13 is pressed into sleeve 14, puncturing seal 20 on inside end 30 of cannula 16. The internal vacuum draws the sample 29 into container 13. Specimen container 13 is then withdrawn from sleeve 14, punctured closure 20 contracting elastically to close the seal. Needle 18 and sleeve 14 are then withdrawn together, and inserted into remover 10 as shown in FIGS. 1 and 3.

Figure 5:
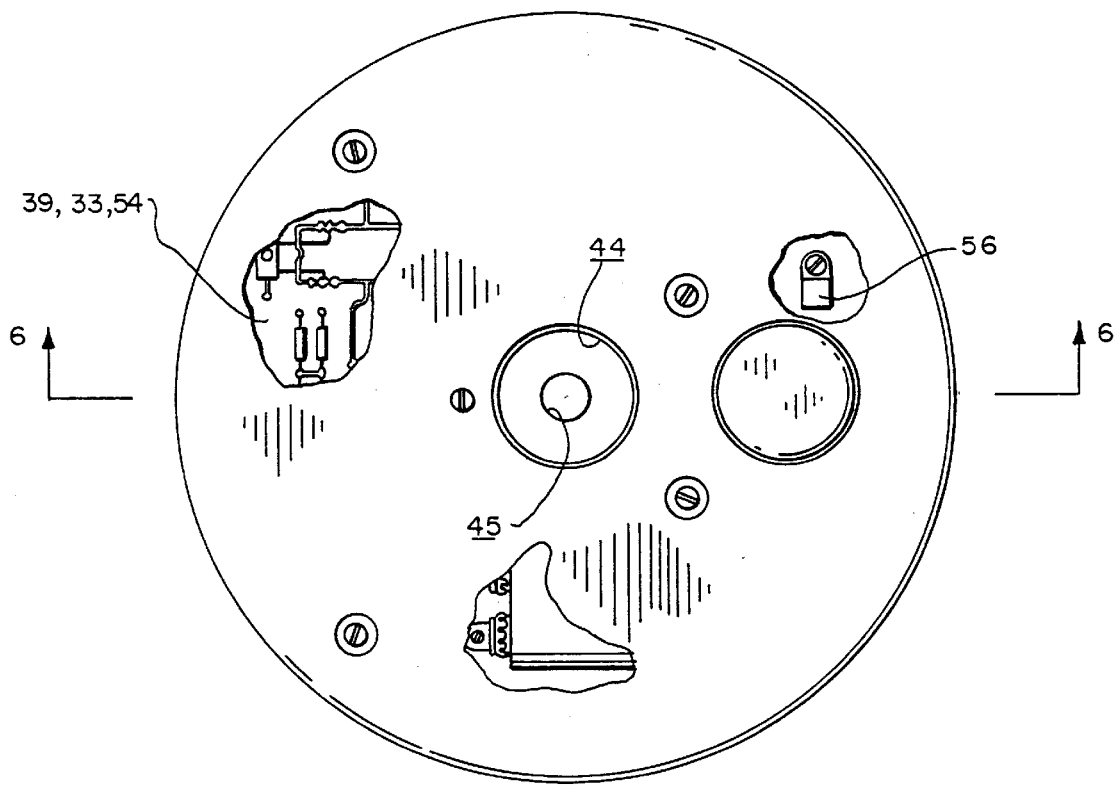

Needle remover 10 comprises a direct current stepper motor 31 (such as Haydon Switch & Instrument, Inc., series 33700), batteries 32, a motor controller (chip) 33 (FIGS. 5 and 10) and a needle insertion block 34, all mounted upon a base plate 35. Screws 36 act through tabs 37 to secure needle block 34 to plate 35. Cover 38 is apertured to accommodate motor 31, and needle insertion block 34. Motor controller 33 is installed upon a panel assembly 39, with other circuit elements described hereinafter. Panel 39 is secured to base plate 35 beneath cover 38. Cover rim 40 is preferably shaped to fit upper rim 41 of receptacle mouth 42. Spring clips 43 secure cover 38 and the entire assembly 10 detachably to receptacle 11.

Needle insertion block 34 has a sleeve insertion bore 44 concentric with a nipple-accepting bore 45. An initiation switch 46 in needle block 34 is spring loaded to normally open position. It is actuated by the tapered shoulder 24 of vacuum container sleeve 14, causing motor 31 to operate.

Cogs 47 of wheel 48 on output shaft 49 of motor 31 engage knurls 28 of needle hub 17. (FIGS. 3 & 6–9) A cog free recessed portion 50 allows unimpeded insertion of needle end 18, sleeve nipple 25 and needle hub 17 through needle block bore 44 and nipple bore 45. As subsequently described, wheel 48 is made to stop with recess 50 adjacent to nipple bore 45 after each use of needle remover 10.

When switch 46 is closed by shoulder 24 of sleeve 14, motor 31 rotates cog wheel 48 to engage knurls 28 by the teeth 47 to unscrew needle assembly 15 from nipple 25. Clearance above cog teeth 47 varies progressively, along wheel periphery 51, to avoid binding with hub 17 as it is screwed progressively out of nipple 25. When hub threads 27 are free of nipple threads 26, needle assembly 15 falls into receptacle 11 hub knurls 28 immediately disengage from cogs 47. If hub flange 52 hangs up on the upper sides 53 of cogs 47, it is freed by continued rotation of wheel 48, recess 50 then coming into position to provide ample clearance.

Figure 10:
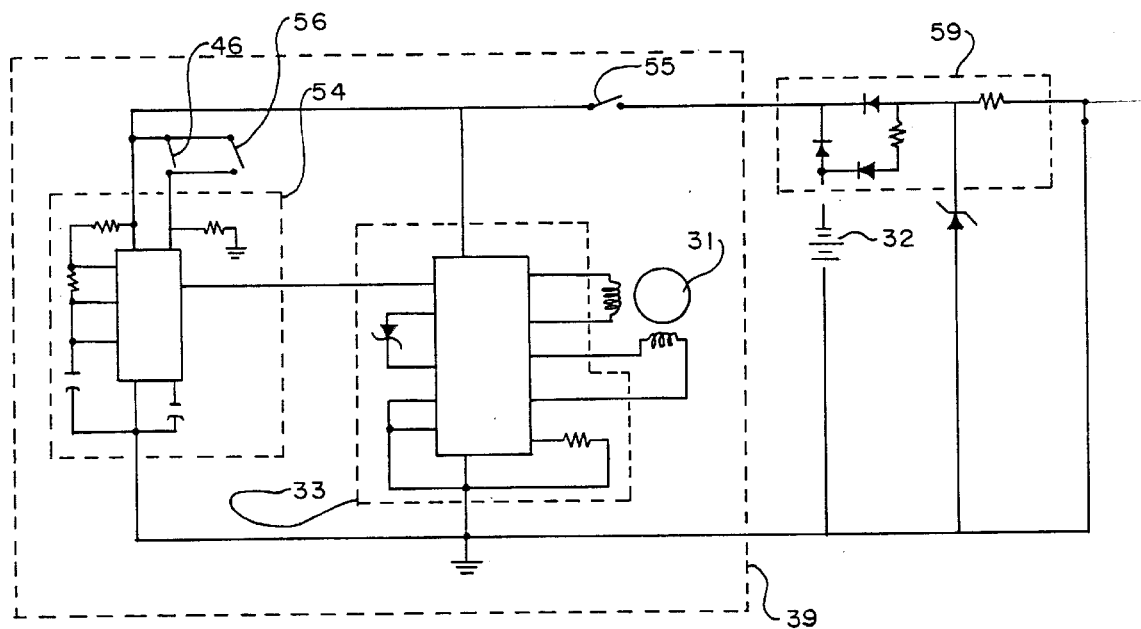

When sample container sleeve 14 is removed from bore 44, motor 31 does not stop until wheel 49 is rotated to bring recess 50 into position for the next use of device 10. Electrical schematic FIG. 10 illustrates a preferred electrical control system. Key elements of the system are provided in control panel assembly 39. Motor controller circuit 33 passes current to DC stepper motor 31 from a source of direct current power, e.g. batteries 32. Controller 33 is programmed to pass current upon command signals from a timing circuit ("clock") 54 which, advantageously, may be a square wave pulse generator.

Figure 4:
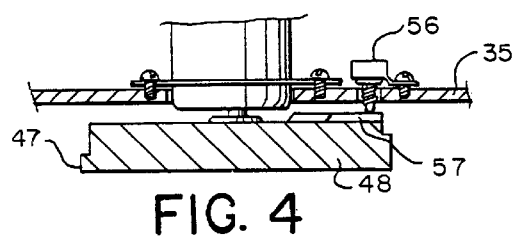
Figure 6:
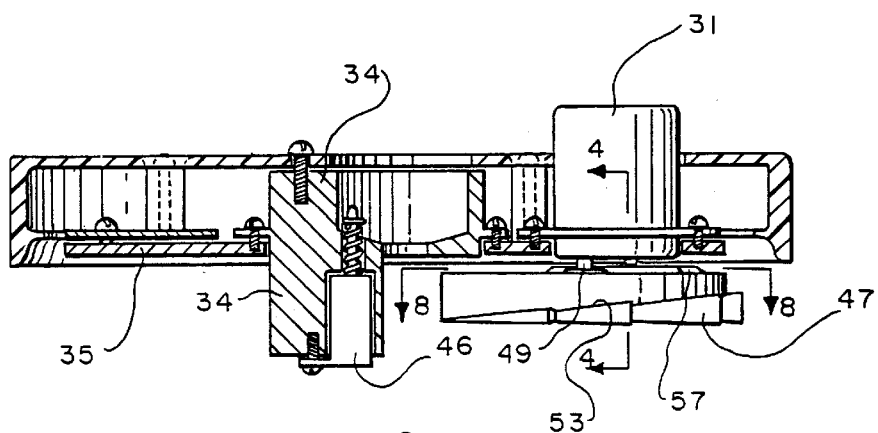
Figure 7:
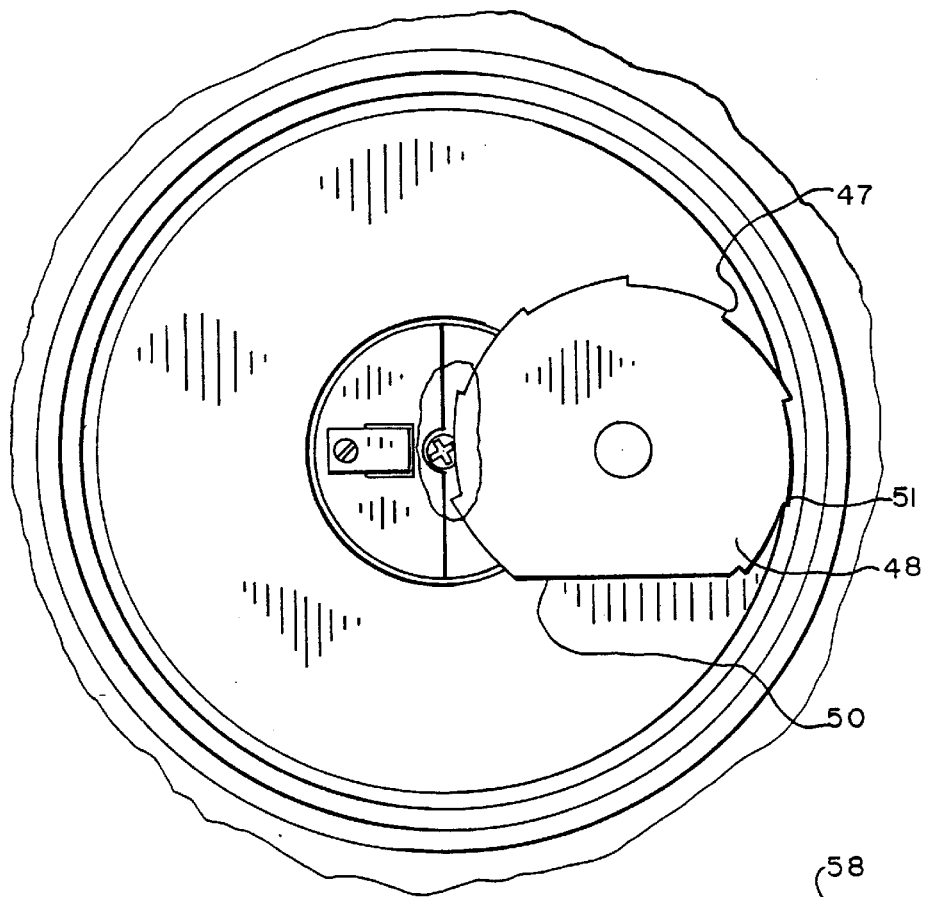
Figure 8:
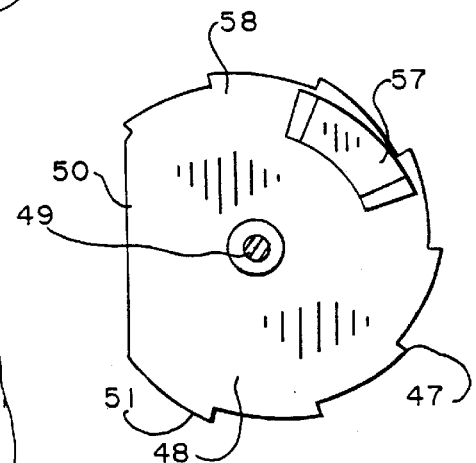
Figure 9:
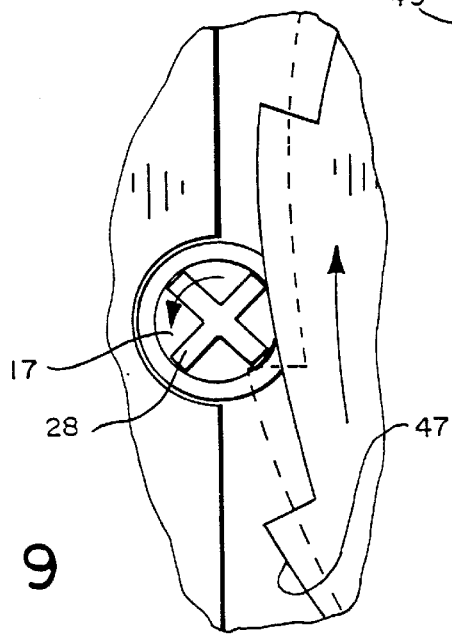

Closing of power supply switch 55 readies needle remover 10 for use. Depression of initiation switch 46 activates clock 54 to generate evenly spaced periodic command signals to motor controller 53. As long as initiation switch 46 is held in closed position by shoulder 24 of sleeve 14, motor 31 continues to operate, rotating cog wheel 48. A cycle control switch 56 is connected in parallel to initiation switch 46. Spring loaded, normally closed switch 56 is mounted on base plate 35, and is controlled by a cam 57 ramped upwardly from top surface 58 of cog wheel 48. (FIGS. 4, 6 and 8)

When initiation switch 46 is released to open, still closed cycle switch 56 causes motor 31 to continue turning until recess 50 is in proper position adjacent the needle removal site. (FIG. 8) In this position, cam 57 opens cycle switch 56, stopping motor 31 and cog wheel 48.

A circuit 59 may be provided for recharging batteries 32. (FIG. 10) This recharging circuit may be provided separately if too large or heavy for mounting upon base plate 35. Or, if desired because of such mounting restraints, a separate DC rectifier/transformer power pack 60 may be provided in lieu of the batteries 32. (FIG. 1)

Figure 11:
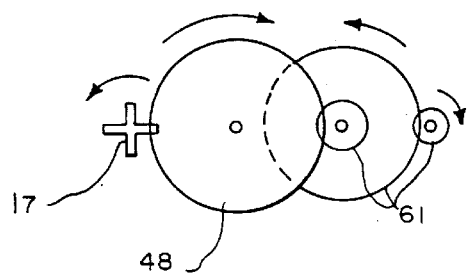

Other changes may be made to the illustrated preferred embodiment of the needle removal device 10 without departing from the spirit of the invention. The wheel 48 could be mounted to revolve about an axle provided on plate 35, to be driven by a train of two or more gears 61 (FIG. 11). The cogs 47 could be replaced with, e.g., a wheel periphery adapted to unscrew hub 17 by friction. Electrical motors 31 other than the preferred DC stepper type described could, with suitable gearing and control features, by utilized.

Figure 13:
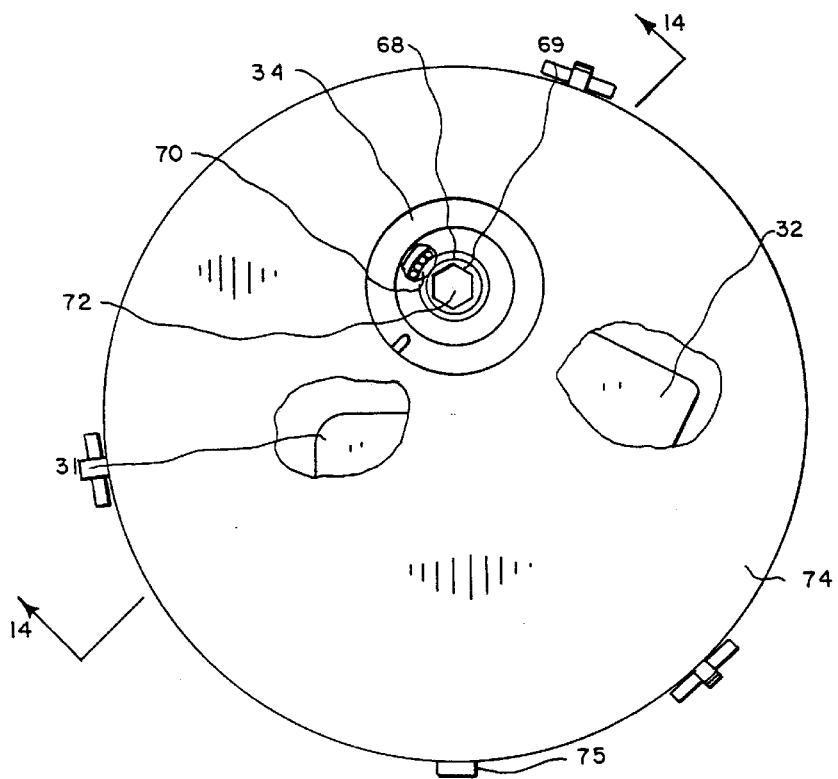
Figure 12:
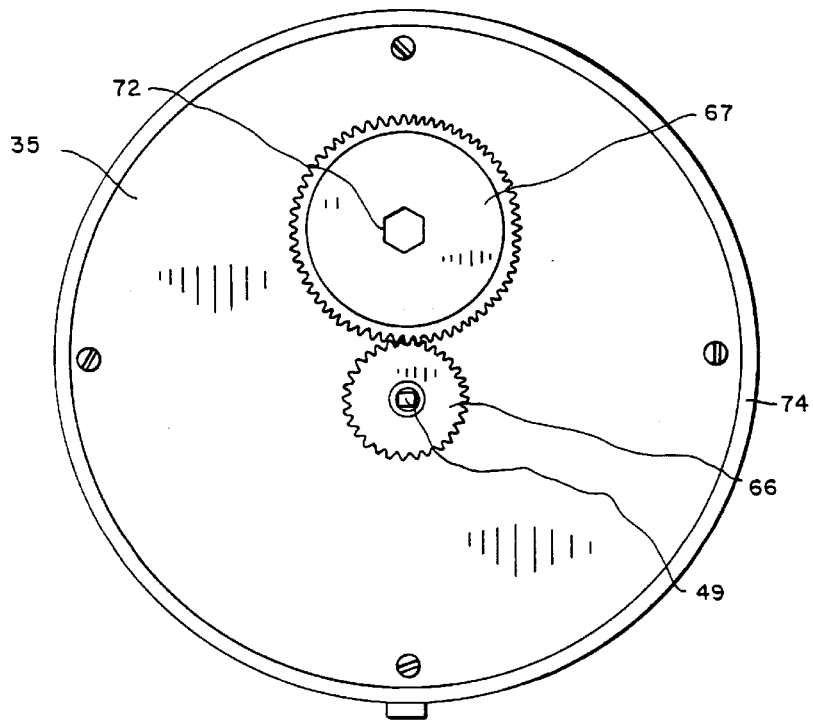
Figure 14:
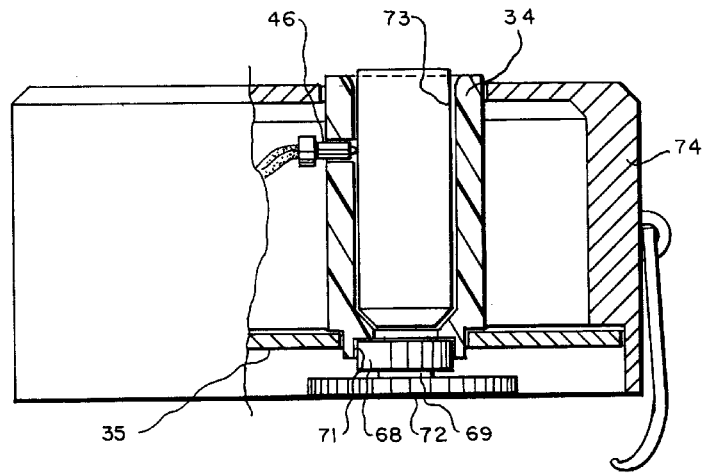

Such an embodiment of needle remover 10, illustrated in FIGS. 12–15, employs a standard direct current motor 31. Cog wheel 66, mounted on motor output shaft 49, engages a second cog wheel 67 secured to open centered bearing 68. An upstanding hub 69 on cog 67 is press fitted into race 70 of bearing 68, (FIGS. 13 and 14). Bearing 68 is secured to needle insertion block 34 by press fitting into a bore 71. Block 34 is secured to base plate 35. A hexagonal hub engaging orifice 72 is provided centrally through hub cog 69. Orifice 72 could be of cruciform shape, e.g., as may be required by needle hub configuration. Normally closed spring loaded switch 46 is mounted in sleeve bore 44 for actuation by the side of sampling sleeve 14. A disposable flexible liner 73 may be provided in sleeve bore 44 to reduce contamination by used canullae 16. A cover 74 may be provided, carrying an electrical connection plug 75.

Figure 15:
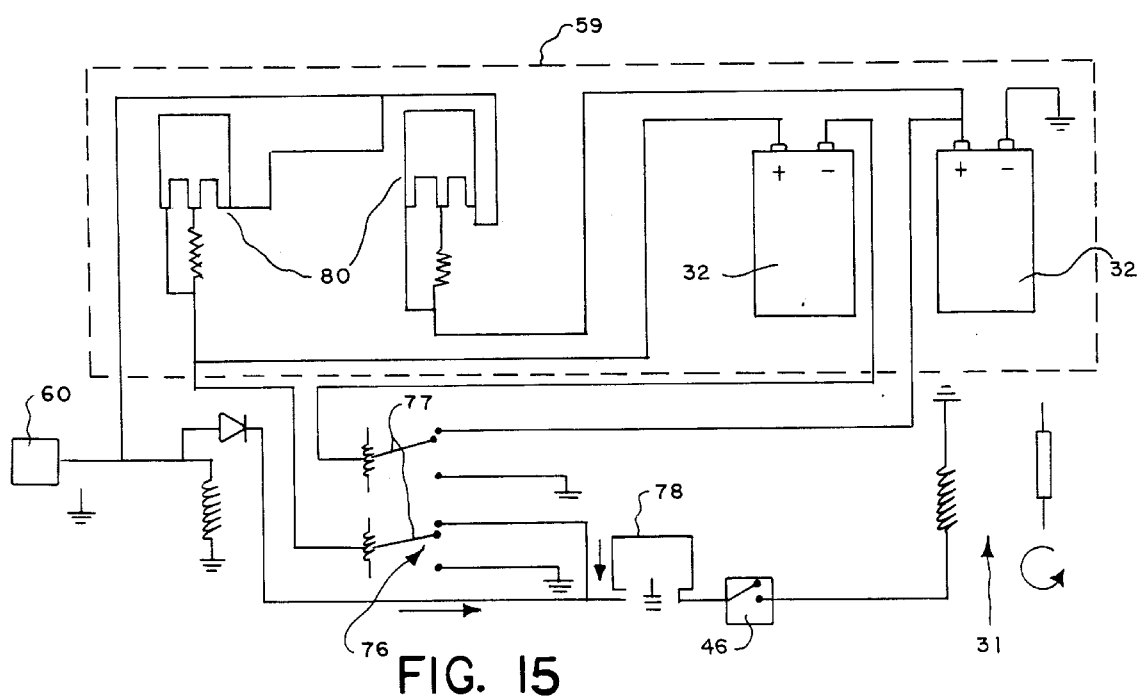

In FIG. 15 a suitable electrical circuit is illustrated for this embodiment of needle remover 10, providing for operation either with batteries 32 or rectifier/transformer 60. Also included is a battery recharge circuit 59. For battery operation, relay 76 operates double pull, double throw switches 77 to connect batteries 32 and motor 31 in series. Voltage regulator 78 controls the voltage applied to motor 31. When alternating current is utilized with rectifier/transformer 60, diode 79 allows direct current voltage to be applied to motor 31 directly from transformer 60, the voltage again controlled by regulator 78. At the same time, relay 76 actuates switches 77 so that transformer voltage is applied to batteries 31 in parallel through current regulators 80. The charging circuit is also operational when motor control switch 46 is open.

To dispose of receptacle 11 with accumulated contaminated needles, needle remover 10 is detached from container mouth 42 by release of spring clamps 43. (FIGS. 1, 3 & 14) Advantageously, an auxiliary lid 62 is provided secured by flexible strip 63 to a retainer band 64 about receptacle opening 42. Auxiliary lid 62 snaps into mouth groove 65. (FIGS. 1 and 3) Needle remover 10 may be quickly installed by clamps 43 upon a new receptacle 11. Device 10 may also be adapted for use with other sizes and types of used needle receptacles.

Figure 24:
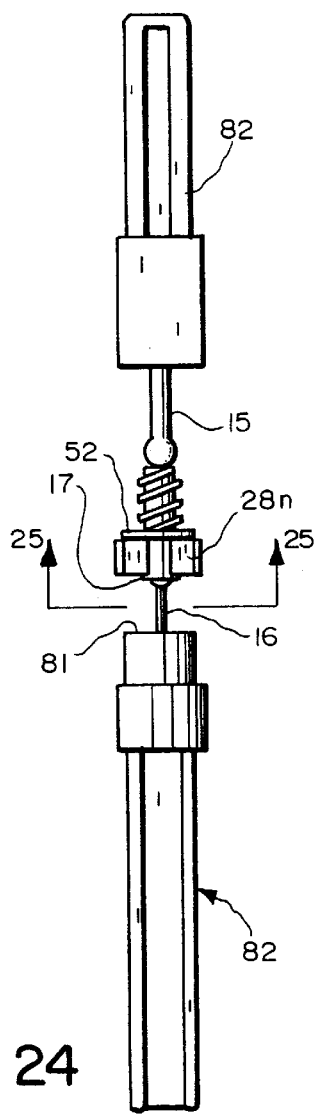
Figure 25:
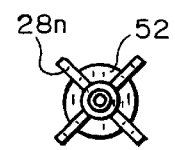

State of the art needle assemblies are not well adapted for manually untouched removal using the device as illustrated in FIGS. 12–15. Current needle hub designs have finger-grip knurls or ribs 28 radially outstanding from the hub body and running parallel to the cannula 16. (FIG. 16) The hub 17 terminates at its upper end in a hub flange disc 52 molded integrally with the ribs and the body of the hub, and extending radially to or beyond the edges of the ribs 28. The disc 52 anchors and strengthens the ribs and provides a flat upper surface which may be tightened against the bottom surface of the nipple 23 of the barrel sleeve 14. However, its main function is to provide a stop against the end 81 of the protective case 82 in which the needle assembly is stored. The radially protruding disc 52 prevents the free passage of the needle assembly 15 through the gripping aperture 72 (FIGS. 12 and 13), or any other simple wrenching device which may be employed for needle removal. The embodiment of needle remover 10 illustrated in FIGS. 1–11, employs a complexly configured cog wheel 48 with a recess 50, along with other features, all to avoid hangup of flange 52 after needle assembly 15 is unscrewed from nipple 23. In contrast, inventive needle assembly 10n, with hubs 17n as illustrated in FIGS. 18–23 may freely fall through gripping aperture 72, for example. Hubs 17n are configured to avoid radial projection of any part thereon beyond the point on the portion of its surface 83 used for wrenching which is closest to cannula 16, including, of course, all points upon the uppermost threaded portion. For efficient gripping and removal, hub 17n may be shaped on its gripping portion hexagonally or in any other convenient or desired configuration. Ribbed shapes similar to state of the art gripping surfaces could be employed as could cylindrical shapes with wrenching flats, and the like. (FIGS. 18–23) In FIGS. 24 and 25, an altered conventional hub is shown, in which the flutes 28 are extended radially beyond the problem-causing disc 52, allowing removal by a square tool engaging only the tips of the flutes 28. The hub configuration may vary somewhat depending upon the type of tool used for its removal from the nipple. For example, for open-ended type tools, rather than those incorporating a complete closed hub-engaging aperture, the portion of the hub below the gripping surface may of course extend farther radially since no interference with the tool would result, as the needle is inserted horizontally. Such a tool is currently incorporated into lids of disposal receptacles, as discussed in the background section. The inventive concept of the hub may of course be adapted equally well to hub designs which may have internal rather than external threads to grip the barrel nipples which may incorporate external rather than internal threads.

Figure 26:
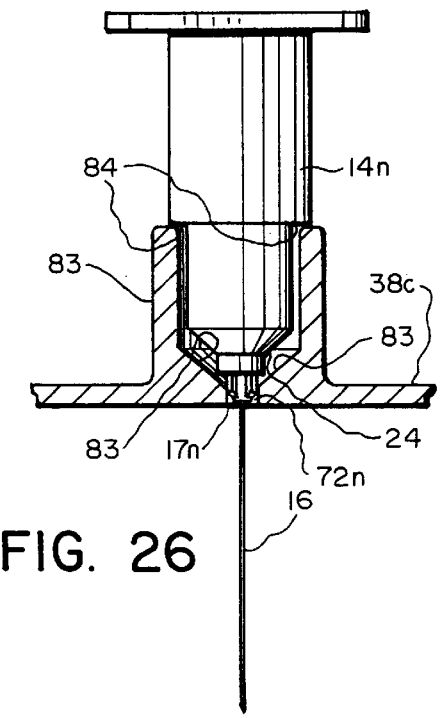
Figure 27:
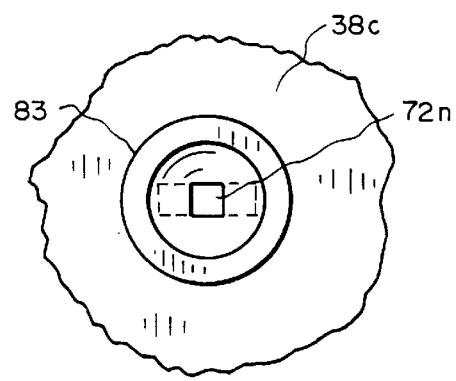
Figure 28:
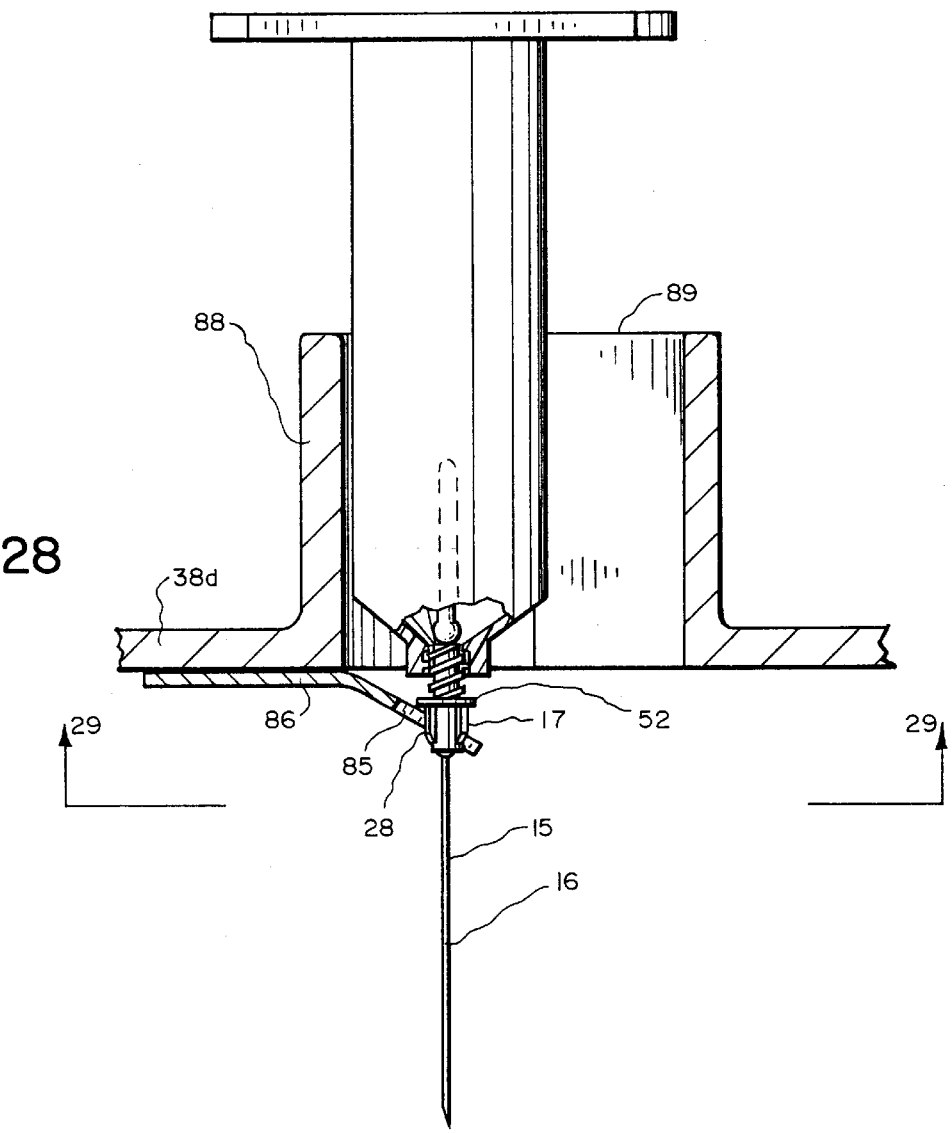

Cooperating lid assembly 38c incorporates an upstanding tube 83 which supports container sleeve 14 while it is manually rotated to unscrew needle hub 17n. Hubs 17n are inserted into a hub engaging bore 72n. (FIGS. 25 and 26) Bore 72n may be square, or, advantageously, rectangular, facilitating needle and hub insertion. Dash lines,FIG.26. Container sleeve 14n, preferably has an upper shoulder 84 preventing contact of lower shoulder 24 with tapered, needle guiding, bottom 83 of tube 83, often contaminated by needle cannula 16. Lid 38c may be used upon disposal containers 11 with either sloping or horizontal tops.

Another cooperating lid assembly 38d utilizes an open-ended needle removal slot 85, carried by a downwardly angling plate 86 secured to lid bottom surface 87, for removal of conventional needle assemblies 15 with conventional hub 17, flutes 28, and disc 52. Container sleeve 14 is rotated by hand to unscrew needle 15, while the tips of flutes 28 are engaged by the sides of slot 85. Then, upon upward removal of container sleeve 14, needle 14 slides or tumbles under gravity downwardly out of slot 85 into the disposal container 11. No sideward movement of needle 15 need be imparted, as is necessary with prior art lid needle removal slots, to free it to fall out of slot 85.

Preferably, lid 38d also incorporates a container sleeve support tube 88, similar to tube 83 of lid 38c, to facilitate its manual rotation. Tube 88 may be circular, but preferably has a lobe 89 opposite slot 85, to provide clearance, should needle assembly 15 tumble instead of sliding from slot plate 86. Support tube 88 assures that container sleeve 14 is removed by lifting directly vertically, to avoid any binding causing needle 15 to inadvertently also be withdrawn.

Figure 29:
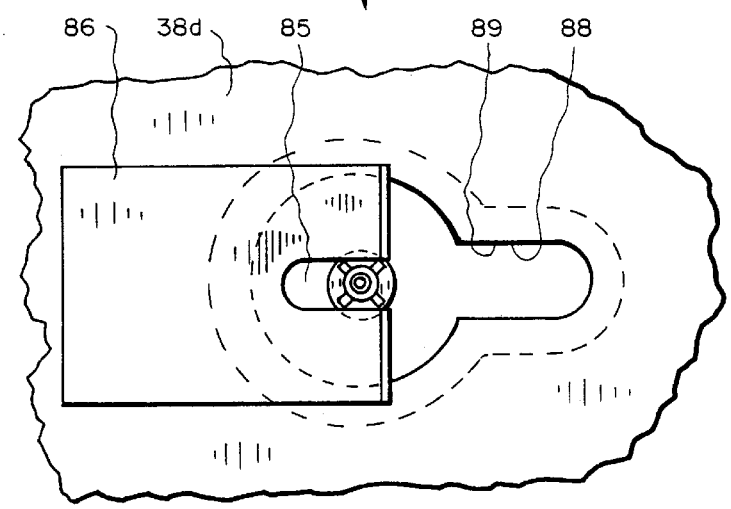
Figure 30:
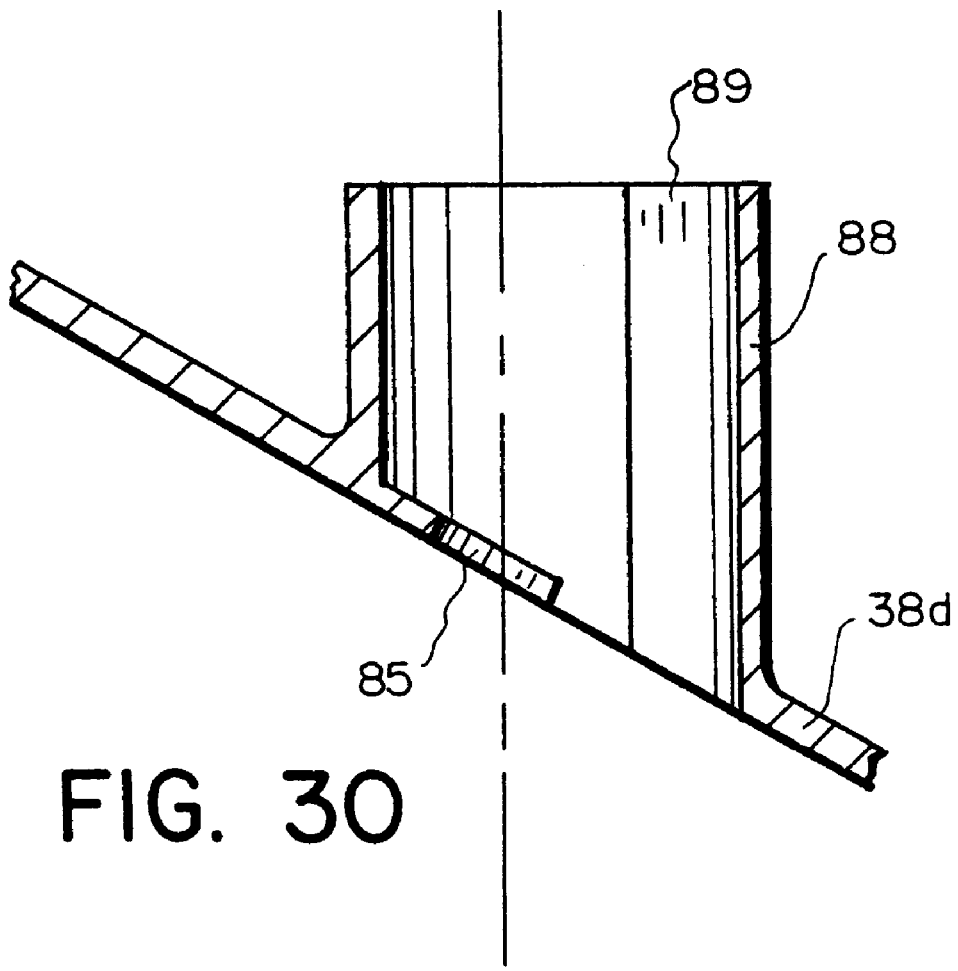

Lid 38d may be adapted for use with disposal containers 11 having sloping tops, as illustrated in FIG. 1. Slot plate 86 may by chance even be parallel to already sloping lid bottom surface 87. In this event it may be possible to form slot 85 directly into lid 38d, eliminating separate plate 86. It is emphasized, however, that it is highly important that support tube 88 be vertical. (FIG. 29)

Figure 31:
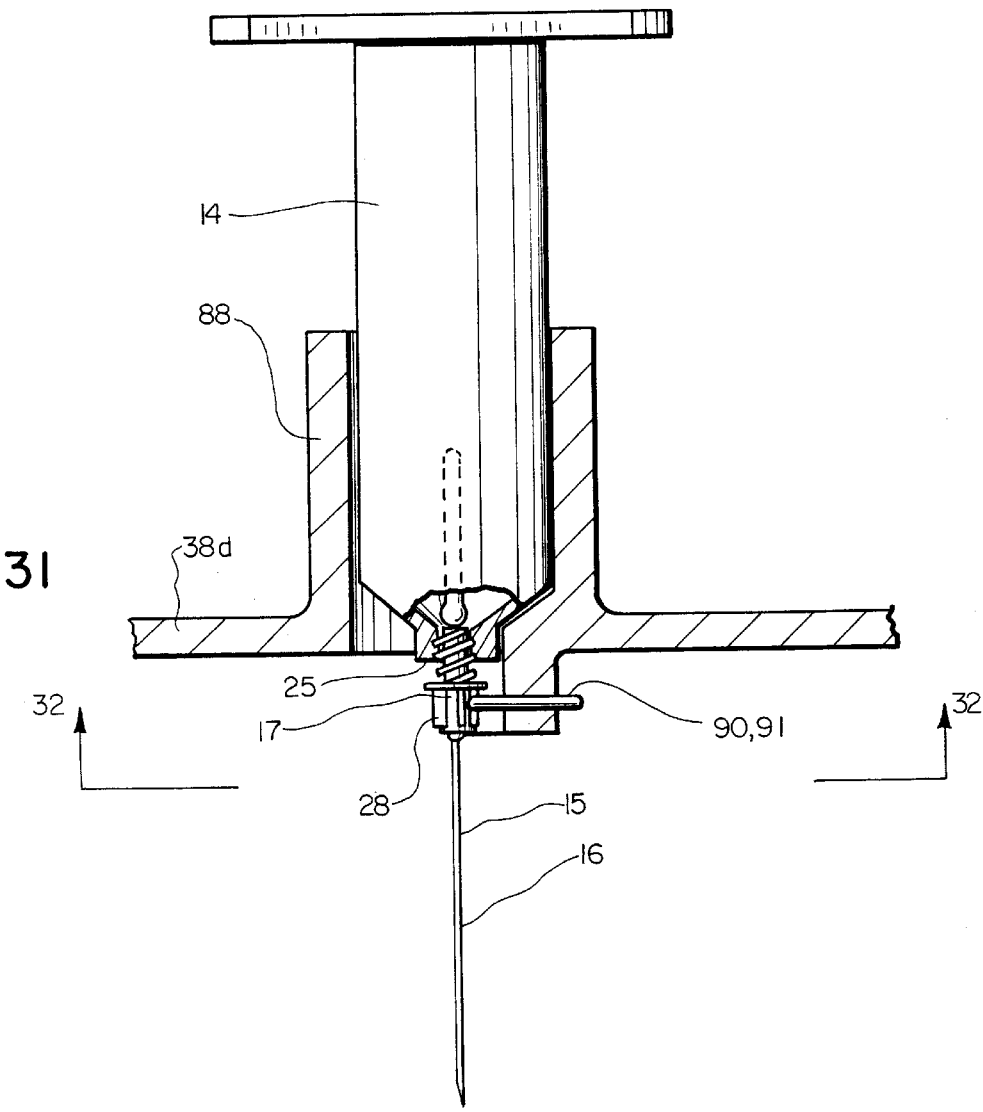
Figure 32:
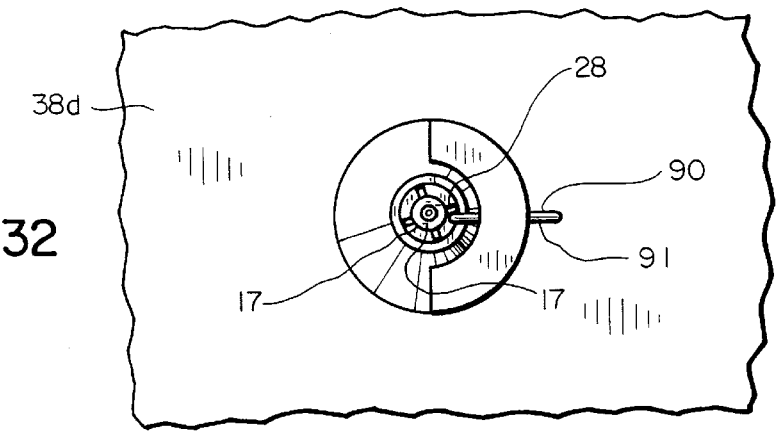
FIG. 32 a bottom plan view of the fragment of FIG. 31.
Figure 33:
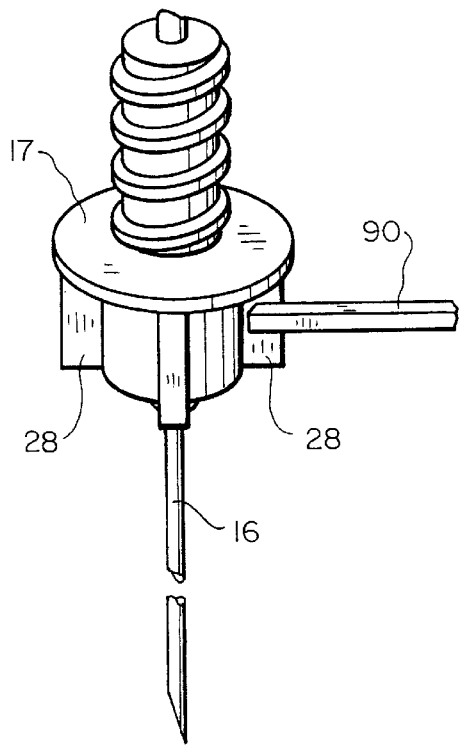
FIGS. 33, 34 and 35, each being a fragmental view showing another embodiment of the hub wrenching member, drawn to an enlarged scale.
Figure 34:
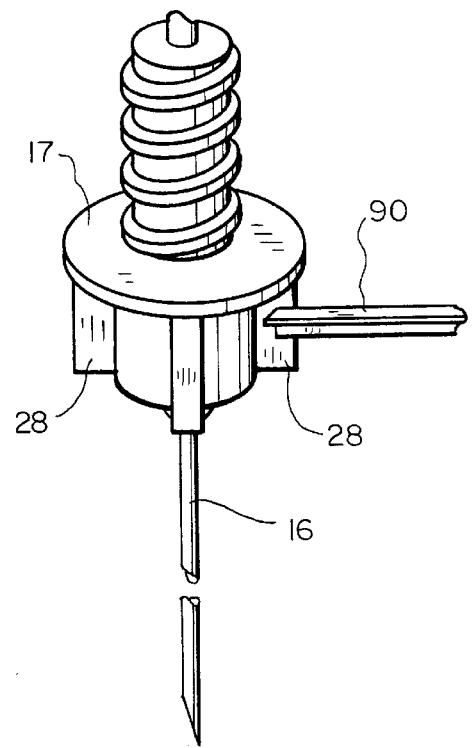
Figure 35:
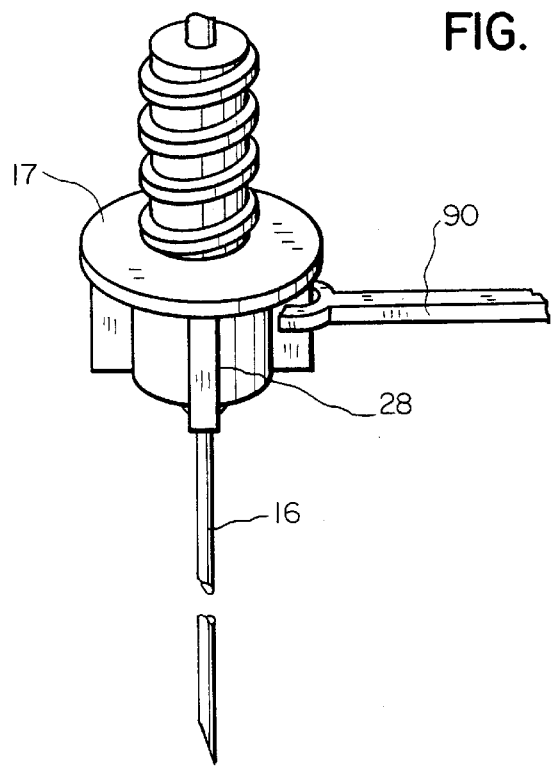

Another cooperating lid assembly 38d utilizes, instead of a downwardly angled slot plate, a wrenching member 90 in the form of a pin 91 mounted to extend horizontally to engage hub 17 between flutes 28. (FIGS. 31 and 32) When barrel 14 is rotated, pin 91 acts against one of the flutes of hub 17 to hold the hub stationary while nipple 25 is unscrewed. Subsequent raising of barrel 14 from guide tube 88 releases the needle assembly to fall into the disposal container. The guide and support tube 88, or some equivalently functioning structure,is necessary to hold the barrel 14 vertical to assure placement of the end 92 of pin between flutes. Among other possible configurations of the wrenching member 90 are those indicated in FIGS. 33, 34, and 35, being rectangular, blade and forked configurations,the latter engaging one of the flute tips thereabout.

The invention may be embodied in still other specific forms without departing from the spirit or essential characteristics thereof. The present embodiments are, therefore, to be considered as illustrative and not restrictive, the scope of the invention being indicated by the appended claims rather than by the foregoing description and all changes that come within the meaning and range of equivalency of the claims are therefore intended to be embraced therein.

What is claimed and desired to be secured by United States Letters Patent is:

1. A device for removal and disposal of a needle assembly with a hub threadably engaging a threaded nipple of a barrel sleeve of a body fluid specimen sampling assembly, said hub having a lowermost portion comprising at least one flute outstanding in a plane radial and longitudinal to the needle of said needle assembly, said device comprising:

a disposal container closed by a lid upwardly thereon, the lid comprising a plate member covering an opening in the disposal container, a perforation through the plate member, a hub wrenching member which comprises a circular pin carried by the plate member extending substantially horizontally partially across the perforation positioned to engage the radially extending side of the flute of the needle assembly when placed downwardly thereinto, so that said needle assembly may be removed from the barrel sleeve by rotation of said sleeve; and means carried by the lid for supporting the barrel sleeve vertically aligned with the lid perforation and the flute engaging wrench member.

* * * * *